United States Patent
Lee

(10) Patent No.: US 7,107,089 B2
(45) Date of Patent: Sep. 12, 2006

(54) AUTOMATED PLANNING VOLUME CONTOURING ALGORITHM FOR ADJUVANT BRACHYTHERAPY TREATMENT PLANNING IN SARCOMA

(75) Inventor: Eva K. Lee, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 432 days.

(21) Appl. No.: 10/465,341

(22) Filed: Jun. 19, 2003

(65) Prior Publication Data
US 2003/0216640 A1 Nov. 20, 2003

Related U.S. Application Data

(62) Division of application No. 09/872,118, filed on Jun. 1, 2001, now Pat. No. 6,615,070.

(60) Provisional application No. 60/208,608, filed on Jun. 1, 2000.

(51) Int. Cl.
*G01B 5/26* (2006.01)
*G01B 13/20* (2006.01)
(52) U.S. Cl. .................. 600/424; 702/19; 702/156
(58) Field of Classification Search .............. 702/19, 702/156; 600/424
See application file for complete search history.

(56) References Cited

OTHER PUBLICATIONS

Delannes, M., M.D., et al., "Low-Dose-Rate Intraoperative Brachytherapy Combined With External Beam Irradiation in the Conservative Treatment of Soft Tissue Sarcoma," Int. J. Radiation Oncology Biol. Phys., vol. 47, No. 1, pp. 165-169, 2000.

Donaldson, Sarah S., M.D., et al., "A Multidisciplinary Study Investigating Radiotherapy in Ewing's Sarcoma: End Results of POG #8346," Int. J. Radiation Oncology Biol. Phys., vol. 42, No. 1, pp. 125-135.

Fujita, Minoru, D.D.S., et al., "Interstitial Brachytherapy for Stage I and II Squamous Cell Carcinoma of the Oral Tongue: Factors Influencing Local Control and Soft Tissue Complications," Int. J. Radiation Oncology Biol. Phys., vol. 44, No. 4, pp. 767-775, 1999.

Fung, Albert Y. C., Ph.D., et al., "Treatment-Plan Optimization for Soft-Tissue Sarcoma Brachytherapy Using a Genetic Algorithm," Int. J. Radiation Oncology Biol. Phys., vol. 47, No. 5, pp. 1385-1395, 2000.

(Continued)

*Primary Examiner*—Michael Borin
(74) *Attorney, Agent, or Firm*—Thomas, Kayden, Horstemeyer & Risley, LLP

(57) ABSTRACT

A mathematical contouring algorithm that automatically determines the planning volume of a sarcoma prior to designing a brachytherapy treatment plan. The algorithm, utilizing computational geometry, numerical interpolation and artificial intelligence (AI) techniques, returns the planning volume in digitized and graphical forms in a matter of minutes. Such an automatic procedure reduces labor time and provides a consistent and objective method for determining planning volumes. In addition, a definitive representation of the planning volume allows for sophisticated brachytherapy treatment planning approaches to be applied when designing treatment plans, so as to maximize local tumor control and minimize normal tissue complications.

22 Claims, 13 Drawing Sheets

OTHER PUBLICATIONS

Alektiar, Kaled M., M.D., et al., "Morbidity of Adjuvant Brachytherapy in Soft Tissue Sarcoma of the Extremity and Superficial Trunk," Int. J. Radiation Oncology Biol. Phys., vol. 47, No. 55, pp. 1273-1279, 2000.

Alektiar, Kaled M., M.D., et al., "High-Dose-Rate Intraoperative Radiation Therapy (HDR-IORT) for Retroperitoneal Sarcomas," Int. J. Radiation Oncology Biol. Phys. vol. 47, No. 1, pp. 157-163, 2000.

Nag, Subir, M.D., et al., "The American Brachytherapy Society Recommendations for Bracytherapy of Soft Tissue Sarcomas," Int. J. Radiation Oncology Biol. Phys., vol. 49, No. 4, pp. 1033-1043, 2001.

Nag, Subir, M.D., et al., "Intraoperative High-Dose-Rate Brachytherapy for the Treatment of Pediatric Tumors: The Ohio State University Expierence," Int. J. Radiation Oncology Biol. Phys., vol. 51, No. 3, pp. 729-735, 2001.

Yap, Johnny, M.D., et al., "Sarcoma as a Second Malignancy After Treatment for Breast Cancer," Int. J. Radiation Oncology Biol. Phys., vol. 52, pp. 131-1237, 2002.

Merchant, Thomas E., et al., "Brachytherapy for Pediatric Soft-Tissue Sarcoma," Int. J. Radiation Oncology Biol. Phys., vol. 46, No. 2, pp. 427-432, 2000.

Koizumi, Masahiko, M.D., et al., "Perioperative Fractionated High-Dose Rate Brachytherapy for Malignant Bone and Soft Tissue Tumors," Int. J. Radiation Oncology Biol. Phys., vol. 43, No. 5, pp. 989-993, 1999.

AUTOMATED PLANNING VOLUME CONTOURING ALGORITHM FOR ADJUVANT BRACHYTHERAPY TREATMENT PLANNING IN SARCOMA

CROSS-REFERENCE TO RELATED APPLICATION

This application is a divisional of copending U.S. utility application entitled, "Automated Planning Volume Contouring Algorithm for Adjuvant Brachytherapy Treatment Planning in Sarcoma," having Ser. No. 09/872,118, filed Jun. 1, 2001, now U.S. Pat. No. 6,615,070, which is entirely incorporated herein by reference which claims the benefit of Provisional application Ser. No. 60/208,608, filed Jun. 1, 2000.

TECHNICAL FIELD

The present invention is generally related to using computational geometry and numerical interpolation techniques to develop a procedure that automatically outlines the contours of the planning volume for sarcoma tumor beds prior to designing brachytherapy treatment plans for soft-tissue sarcoma.

BACKGROUND OF THE INVENTION

Soft-tissue sarcomas are tumors that arise in the soft tissues that connect, support and surround other parts of the body, such as muscles, tendons, fat, joint linings, and blood vessels. Although about one-half of the cases occur in the arms and legs, soft-tissue sarcomas are known to develop at any site in the body. Sarcoma tumors occur primarily in the second and sixth decades of life, but may occur at any age and, typically, the incidence rises with increasing age and is more prevalent in men.

There are more than fifty different types of soft-tissue sarcomas and sarcoma-like growths, at least thirty-five of which are malignant. Approximately 6,000 new cases of soft-tissue sarcoma are diagnosed each year in the United States. Additionally, the large majority of soft-tissue sarcomas are greater than 5 cm in size, requiring a combination of treatment techniques. Fortunately, soft-tissue sarcomas are relatively rare, representing only about one percent of all cancer cases, but they provide unique challenges in detection and treatment.

In the past, the standard treatment for soft-tissue sarcoma included amputation of limbs or radical surgery. In current practice, soft-tissue sarcomas are typically treated with a more conservative surgery combined with radiation therapy. The surgical removal of the tumor is the primary treatment. However, adjuvant (or additional) treatment with radiation therapy greatly increases the effectiveness of sarcoma treatment. Radiation therapy may be used before, during and/or after the surgical removal of the sarcoma. Typically, treatment involving both surgery and radiation therapy will include external-beam radiotherapy or brachytherapy.

Brachytherapy is an advanced cancer treatment that delivers radiation therapy from within the body (as opposed to external application of radiation to the tumor and surrounding tissues). The benefit of brachytherapy is that a high dose of radiation may be applied to the tumor or tumor bed (where the tumor was removed) while reducing the dose to surrounding healthy tissues.

In application, brachytherapy may be used to treat soft-tissue sarcomas in two ways. In one approach, during surgery, after the surgeon removes the tumor, the radiation oncologist implants a series of catheters into the tumor bed. Several days after the operation, radiotherapeutic seeds are inserted into each of these catheter tubes. These seeds stay in the catheter tubes for several days, delivering a high dose of radiotherapy to the area of the tumor. When the treatment is completed, both the radiotherapeutic seeds and the catheters are removed. The second form of brachytherapy is called high dose rate intra-operative radiation therapy. In this procedure, all the radiotherapy is actually delivered during the operation. This procedure requires a specially shielded operating room where both the surgery and the radiation therapy can be given. However, the high dose rate approach often requires a subsequent course of external beam radiation therapy.

The form of adjuvant brachytherapy in which catheters filled with radioactive seeds are inserted into the tumor or tumor bed is promising. However, this technique is limited by the difficulties of precisely placing catheter tubes into position and applying the correct amount of radiation to the affected areas while limiting the exposure of "healthy" tissues to the radiation. Several factors contribute to the difficulty of applying this treatment modality to soft-tissue sarcoma. First, each anatomical site and associated patient/tumor geometry is unique. Second, the tumor bed is usually of irregular shape. Third, the catheters, inserted during surgery, are often non-uniformly spaced and non-coplanar. Any of these factors may result in over or under treating the affected areas, as well as radiating healthy tissues.

In current practice, the planning volume for adjuvant brachytherapy treatment for soft-tissue sarcoma is typically derived via a tedious manual process, often resulting in the volume of the sarcoma not being appropriately determined. In the manual process, the outline of the volume is determined based on the positions of the catheters by hand calculations and planner observations. The current process for determining the planning volume is subjective, inconsistent, time-consuming, and highly dependent on the human planner. Thus, the current methods for determining the planning volume of sarcomas for brachytherapy may result in variability in the placement of the radiation seeds inside the catheters and variability in the distribution of radiation to the sarcoma bed.

In order to provide the most effective radiation therapy, the radiation dose distribution must cover all of the tumor bed and at the same time affect as little as possible of the healthy surrounding tissue. The ultimate location of the radiation seeds is one of the most important factors affecting the radiation dose distribution. Since the desired dose distribution is affected by the planning volume and the placement of the catheters and radiation seeds, the accurate derivation of the planning volume is a fundamental problem. The current practice does not provide a consistent, efficient and accurate method for determining the planning volume.

Thus, a heretofore unaddressed need exists in the industry to address the aforementioned deficiencies and inadequacies.

SUMMARY OF THE INVENTION

In order to increase the effectiveness of catheter brachytherapy treatment, the delivery of the radioactive sources to the affected areas (or planning volume) is critical. The present invention focuses on the automated generation of planning tumor volumes for the treatment of soft-tissue sarcomas. By using an automated contouring algorithm the planning tumor volume can be determined and the optimal placement and insertion of radioactive seeds can be designed to provide the most effective brachytherapy treatment.

The present invention provides a system and method for automatically determining the planning volume of a sarcoma by algorithmic manipulation of catheter coordinate input data. Initially, the catheters are inserted into the sarcoma bed during a surgical procedure. The volume of the sarcoma is divided into cross-sectional slices in which the catheters appear as "centers." Around these centers, a circle having a certain radius is drawn. The radius of the circles is an indicator of the area over which the radioactive seeds will provide effective treatment. By configuring the radii of the circles to have sufficient size, the entire surface of each of the cross-sectional slices may be covered and, therefore, treated with the radioactive seeds. Optimally, the circles are configured such that all areas of the sarcoma receive treatment, while only a minimum of healthy tissue is exposed to the radiation.

The automated planning volume algorithm is comprised of a number of subroutines or sub-algorithms. The algorithm, utilizing computational geometry, numerical interpolation, and artificial intelligence (AI) techniques to manipulate the catheter coordinates, returns the planning volume in digitized and graphical forms in a matter of minutes. After the coordinates are inputted, the algorithm will automatically determine the "span," or furthest distance between centers, and order the circles in a normal numerical progression. The algorithm is able to self-correct the numbering of the centers such that a smooth curve is defined which encompasses the affected tissue and limits incorporation of healthy tissue within the curves. Then, the algorithm selects tangent points for each circle and determines the corresponding tangent lines for groups of circles. By iteration of the tangent lines, the algorithm generates a series of curves. These curves provide the overall shape of the surface of each cross-sectional slice. The shapes of the individual slices may then be compiled so as to provide the overall shape and volume of the sarcoma bed. The algorithm outputs the resultant volume data as a graphical representation of the planning volume and the location of the digitized catheter coordinates therein.

The automatic generation of sarcoma planning volumes is a fast and efficient way to consistently and accurately determine planning volumes. Instead, of performing lengthy and difficult calculations by hand, the clinician may simply input the catheter coordinates for each slice, wait a few minutes for the algorithm to compute the data and generate the graphical outputs, and then review and evaluate the outputs. The automated approach provides a definitive representation of the planning volume and will allow for the application of more sophisticated brachytherapy treatment planning designs. Ultimately, the detailed volume graphics and coordinate data will aid in developing treatment plans that maximize local tumor control and minimize normal tissue complications.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Figure 1:
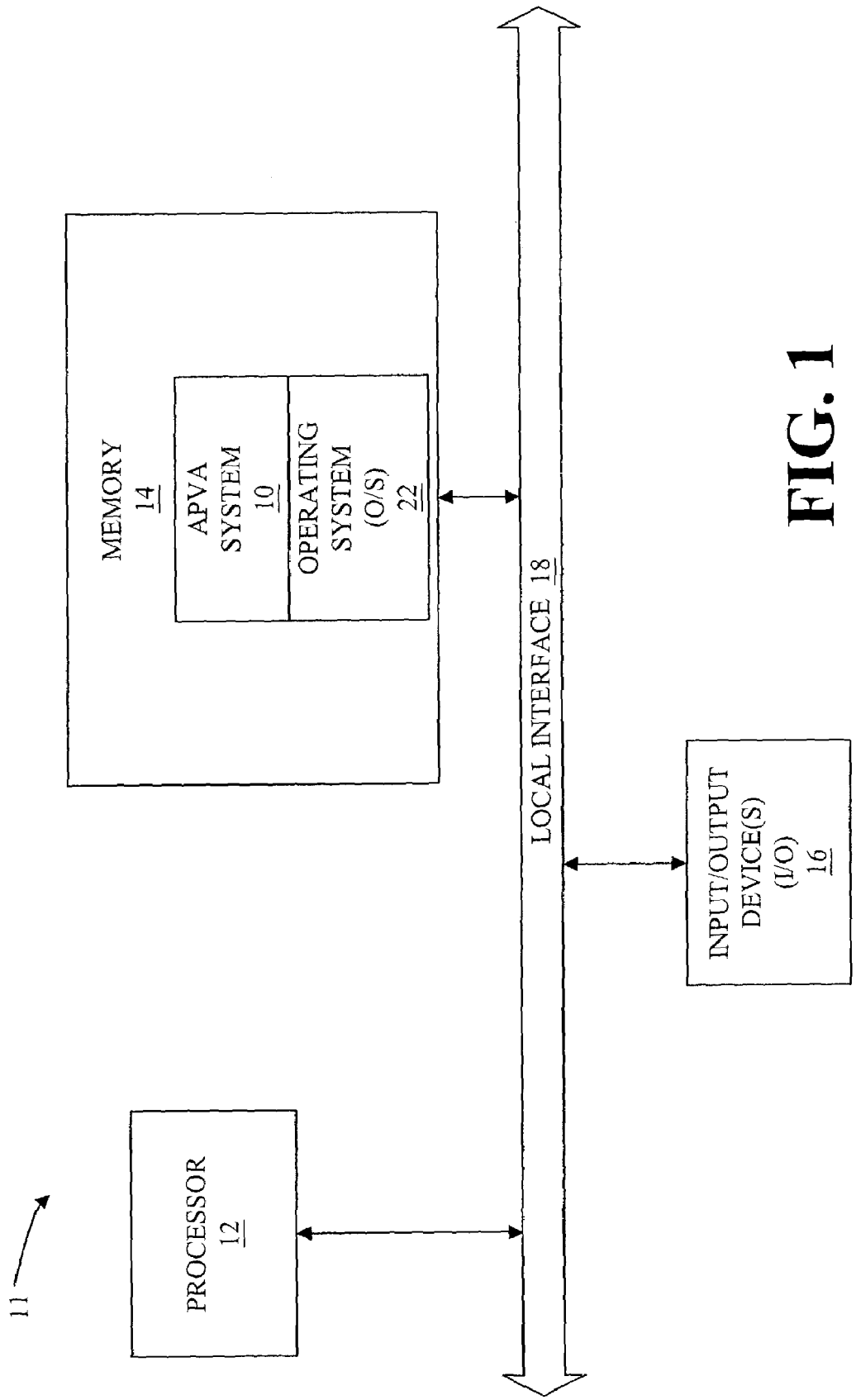
FIG. 1 is a block diagram showing the implementation of the automated planning volume system.

It has been found that accurately determining the planning volume of a sarcoma for radiation treatment can maximize local tumor control and minimize normal tissue complications and damage. The present invention is an automated tumor volume contouring algorithm which utilizes computational geometry, numerical interpolation, and artificial intelligence (AI) techniques to determine the planning volume of a sarcoma.

Briefly described, in architecture, one embodiment of the system, among others, can be implemented as follows. By combining both geometric, numerical and AI interpolation techniques, a mathematical algorithm can be used to automatically generate the planning volume of a sarcoma. The planning volume of a sarcoma can be viewed mathematically as the minimum smoothly connected volume that contains a set of "circles." It is envisioned that the automated planning volume algorithm (APVA) system will be implemented in software, hardware or a combination thereof. The algorithms used to determine the planning volume are contingent only upon a series of digitized data inputs. With these inputs, the APVA system automatically calculates an output of digitized coordinates for the planning volume using a configuration of software and hardware. The actual algorithms performing the calculations are essentially a "black box" to the clinician, who merely inputs the data into the system and then evaluates the outputs.

During a surgical procedure, catheters are placed within the tumor bed and a series of images are taken showing the location of the catheters. Indicators are contained in the catheters to identify their positions and the potential positions of the radioactive seeds. To achieve clarity of seed images and accuracy in seed reconstruction, the patient is positioned so that the catheters are parallel to the gantry axis of rotation of the imaging mechanism. However, in the case where an anatomical site does not allow this, or when the catheters are not all parallel to each other, it is also possible that orthogonal anteroposterior (AP) and lateral films are taken. If there is difficulty in identifying seeds in some of the orthogonal films, oblique film may be needed in order to show all of the seeds. The seed positions are then reconstructed from two films that are less than 90° apart. Although films are mentioned specifically herein, it is envisioned that any means for imaging the sarcoma area may be utilized to provide a pictorial representation of the sarcoma bed and catheter positions.

Catheter and seed positions are reconstructed from the digitization of two films. The algorithm, which "reconstructs" the digital positions for the catheters, compensates for the beam divergence. For every seed position, each film will provide one longitudinal coordinate along the gantry rotation axis. If the patient remains stationary, the longitudinal coordinate will suffice to identify the seed position. However, the patient often moves during the time the two films are acquired; in which case, the final seed position is taken to be the midpoint of the two reconstructed positions. The difference between the two positions defines the localization error, which is normally set to a limit ranging from 0.2 to 0.5 cm. The seed reconstruction is verified by comparing a computer-generated picture of seed positions with the corresponding simulation film. The clinician will determine that the final seed position is acceptable when the localization error is less than approximately 0.2 cm after demagnification.

The target volume, or planning volume, of the sarcoma is defined to be the slab of tissue r cm perpendicularly away from the curvilinear plane defined by the mesh of catheters. If adjacent catheters are separated by more than 2 r cm (or 1 cm), the tissue between the two catheters is assumed to be a part of the tumor bed. The point of intersection of a catheter and a cross-sectional slice is referred to as a "center." Each center has an associated circle about it with a radius r. Typically, the radius r is taken to be 0.5 cm. The input data for the algorithm consists of the digitized coordinates of the catheter positions in each of the cross-sectional slices of the tumor bed and the estimated distance r from the catheters to the tumor surface.

Mathematically, one can view the planning volume as a minimum smoothly connected surface which contains a set of circles, each circle centered at a given catheter position in a given cross-sectional slice. The algorithm performs local interpolation on consecutive triplets of circles, and returns the planning volume in a matter of minutes.

Viewing each slice as a two-dimensional surface, the algorithm begins by labeling the centers in each slice in a "natural" order. The shape formed by following the associated circles in the specified order provides the overall shape of the tumor bed within the given slice. The algorithm then seeks to form a smoothly connected body that compactly encapsulates the shape of the tumor bed. The algorithm will perform well regardless of whether the catheters are all close together (with the target, a volume mass), the catheters are spread far apart in the plane, or the catheters are arranged in a convoluted way. The performance of the algorithm is measured by the algorithm's ability to automatically generate clinically acceptable smoothly connected surfaces for anatomical sites of different shapes.

Visually, one can think of the algorithm as constructing an "inner curve" and an "outer curve" tangent to the ordered collection of circles. Construction of these curves requires the determination of tangent points followed by local interpolation. The algorithm works the same for determining both the outer-curve and inner-curve.

More particularly, the APVA system can be described as a series of algorithmic steps that determine the planning volume of a sarcoma bed from digitized catheter data and a given r. Following the surgical implantation of catheters into the sarcoma bed, the coordinates of the catheters are digitized and each "sphere" of a specified radius is centered at a given catheter position. The sarcoma bed is then divided into a number of cross-sectional slices. When viewed as cross-sectional slices, the catheter positions are the centers of circles with a specified radius r. The point of intersection of a catheter and a cross-sectional slice is referred to as a "center," each of which has a corresponding radius r.

The digitized coordinates of the catheters and the corresponding radii for each of the cross-sectional slices of the tumor bed comprise the algorithm inputs. The first step of the algorithm is to find the "span" of the circles by locating the two centers, the origin and the destination, that are the furthest apart. Starting at the origin, the algorithm engages in a two-phase procedure of locating and labeling, from left to right, the centers in a "natural" order. The algorithm engages in dynamic local searching and uses a greedy approach to seek out the next-closest center for labeling. If, however, the positions of the catheters and the initial labeling thereof would result in an order of the centers that produces a kink or sharp indentation cutting off part of the sarcoma bed from treatment, the algorithm self-corrects and re-labels and re-orders the centers. Thus, the labeling of the centers and ordering of the circles provides the overall shape of the tumor bed surface.

The second step of the algorithm, the identification of tangent points, is performed after the labeling and ordering step. Based on the order of the centers, tangent points and their corresponding tangent lines are determined for each consecutive pair of circles.

The third step of the algorithm determines whether the middle circle of a group of three consecutive circles may be bypassed. Statistically based artificial intelligence (AI) has shown that the iterations on the circles can sometimes be simplified, and potential kinks removed from the generated curves of the sarcoma surfaces, by removing some of the middle circles from the calculations. For example, if analysis indicates that the middle circle 2 of a triplet of circles 1, 2 and 3 may be bypassed, the algorithm then proceeds to examine circles 1, 3 and 4, wherein circle 3 is now the middle circle, and so forth. Thus, the circles are classified into one of two groups; those circles which may be bypassed or omitted, and those circles which may not be bypassed or must be included in the interpolation. Typically, only a small portion of the circles may be bypassed. The bypassing step is performed twice in conjunction with the local nonlinear interpolation for the inner and outer curves. Thus, a circle may be bypassed in one curve, but included in the other for interpolation purposes.

Following the determination of bypassed circles, step four of the algorithm involves the performance of local nonlinear interpolation on each consecutive pair of tangent lines to give the resultant curved surface of the tumor bed. The interpolation step consists of two phases; a nonintersecting phase, which identifies the non-overlapping tangent line segments, and an intersecting phase, which identifies the intersecting tangent line segments. The local interpolation step is performed twice so as to generate the inner and outer curves of the planning volume for each cross-sectional slice.

The cumulative collection of curves resulting from the local interpolation step specifies the contours of the tumor bed.

From the iterative process of interpolation, the algorithm generates the digitized coordinates and graphical representations that define the planning volume. Finally, the output from the algorithm is evaluated and approved by a clinician.

The present invention can also be viewed as providing methods for mathematically determining the planning volume of sarcoma so as to produce improved brachytherapy treatments. In this regard, one embodiment of such a method, among others, can be broadly summarized by the following steps: insertion of catheters into the sarcoma bed; obtaining a series of images indicating the position of the catheters; digitization of the catheter images; generation of the planning volume and digital positions of the catheters within the planning volume; and comparison of the generated positions with the positions shown on the images. The generation of the planning volume and the digital catheter positions is accomplished with an automatic contouring algorithm comprising an ordering of circles and labeling of circle centers, identification of tangent points, determination of whether middle circles may be bypassed, and local interpolation.

It is anticipated that the Automated Planning Volume Algorithm (APVA) system of the invention can be implemented in software (e.g., firmware), hardware, or a combination thereof. In the currently contemplated best mode, the APVA system is implemented in software, as an executable program, and is executed by a special or general purpose digital computer, such as a personal computer (PC; IBM-compatible, Apple-compatible, or otherwise), workstation, minicomputer, or mainframe computer. As shown in FIG. 1, the APVA system, denoted by reference numeral 10, may be implemented with a general purpose computer.

Generally, in terms of hardware architecture, as shown in FIG. 1, the computer 11 includes a processor 12, memory 14, and one or more input and/or output (I/O) devices 16 (or peripherals) that are communicatively coupled via a local interface 18. The local interface 18 can be, for example but not limited to, one or more buses or other wired or wireless connections, as is known in the art. The local interface 18 may have additional elements, which are omitted for simplicity, such as controllers, buffers (caches), drivers, repeaters, and receivers, to enable communications. Further, the local interface 18 may include address, control, and/or data connections to enable appropriate communications among the aforementioned components.

The processor 12 is a hardware device for executing software that can be stored in memory 14. The processor 12 can be any custom made or commercially available processor, a central processing unit (CPU), an auxiliary processor among several processors associated with the computer 11, a semiconductor based microprocessor (in the form of a microchip or chip set), a macroprocessor, or generally any device for executing software instructions. Examples of suitable, commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc, or a 68APVA series microprocessor from Motorola Corporation. In the preferred embodiment, the APVA system is run on a SUN UltraSparc workstation of 166 MHz.

The memory 14 can include any one or combination of volatile memory elements (e.g., random access memory (RAM, such as DRAM, SRAM, SDRAM, etc.)) and non-volatile memory elements (e.g., ROM, hard drive, tape, CDROM, etc.). Moreover, the memory 14 may incorporate electronic, magnetic, optical, and/or other types of storage media. Note that the memory 14 may have a distributed architecture, where various components are remotely situated from one another, which can be accessed by the processor 12.

The software in memory 14 may include one or more separate programs, each of which comprises an ordered listing of executable instructions for implementing logical functions. In the example of FIG. 1, the software in the memory 14 includes the APVA system and a suitable operating system (O/S) 22. A non-exhaustive list of examples of suitable commercially available operating systems 22 is as follows: a Windows operating system from Microsoft Corporation, a NetWare operating system available from Novell, Inc., or a UNIX operating system, which is available for purchase from many vendors, such as Hewlett-Packard Company, Sun Microsystems, Inc., and AT&T Corporation. The operating system 22 essentially controls the execution of other computer programs, such as the APVA system 10, and provides scheduling, input-output control, file and data management, memory management, and communication control and related services.

The APVA system 10 is a source program, executable program (object code), script, or any other entity comprising a set of instructions to be performed. As a source program, the program requires translation via a compiler, assembler, interpreter, or the like, which may or may not be included within the memory 14, so as to operate properly in connection with the O/S 22. Furthermore, the APVA system 10 can be written as (a) an object oriented programming language, which has classes of data and methods, or (b) a procedure programming language, which has routines, subroutines, and/or functions, for example but not limited to, C, C++, Pascal, Basic, Fortran, Cobol, Perl, Java, and Ada. In the currently contemplated best mode of the invention, the algorithms for the APVA system 10 are written using the SPLUS 5.0 (Vlathsoft; Seattle, Wash.) language. The series of APVA algorithms are automatically executed by the program to calculate the planning volume of a sarcoma bed from a series of digitized catheter coordinate positions.

The I/O devices 16 may include input devices, for example but not limited to, a keyboard, mouse, scanner, microphone, etc. Furthermore, the I/O devices 16 may also include output devices, for example but not limited to, a printer, display, etc. Finally, the I/O devices 16 may further include devices that communicate both inputs and outputs, for instance but not limited to, a modulator/demodulator (modem; for accessing another device, system, or network), a radio frequency (RF) or other transceiver, a telephonic interface, a bridge, a router, etc.

If the computer 11 is a PC, workstation, or the like, the software in the memory 14 may further include a basic input output system (BIOS) (omitted for simplicity). The BIOS is a set of essential software routines that initialize and test hardware at startup, start the O/S 22, and support the transfer of data among the hardware devices. The BIOS is stored in ROM so that the BIOS can be executed when the computer 11 is activated.

When the computer 11 is in operation, the processor 12 is configured to execute software stored within the memory 14, to communicate data to and from the memory 14, and to generally control operations of the computer 11 pursuant to the software. The APVA system 10 and the O/S 22, in whole or in part, but typically the latter, are read by the processor 12, perhaps buffered within the processor 12, and then executed.

When the APVA system 10 is implemented in software, as is shown in FIG. 1, it should be noted that the APVA system 10 can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The APVA system 10 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium may also include paper or another suitable medium upon which the program is printed, since the program is electronically captured, via for instance optical scanning of the paper or other medium, and then compiled, interpreted or otherwise processed in a suitable manner, if necessary, for storage in a computer memory.

In an alternative embodiment, where the APVA system 10 is implemented in hardware, the APVA system can implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 2A:
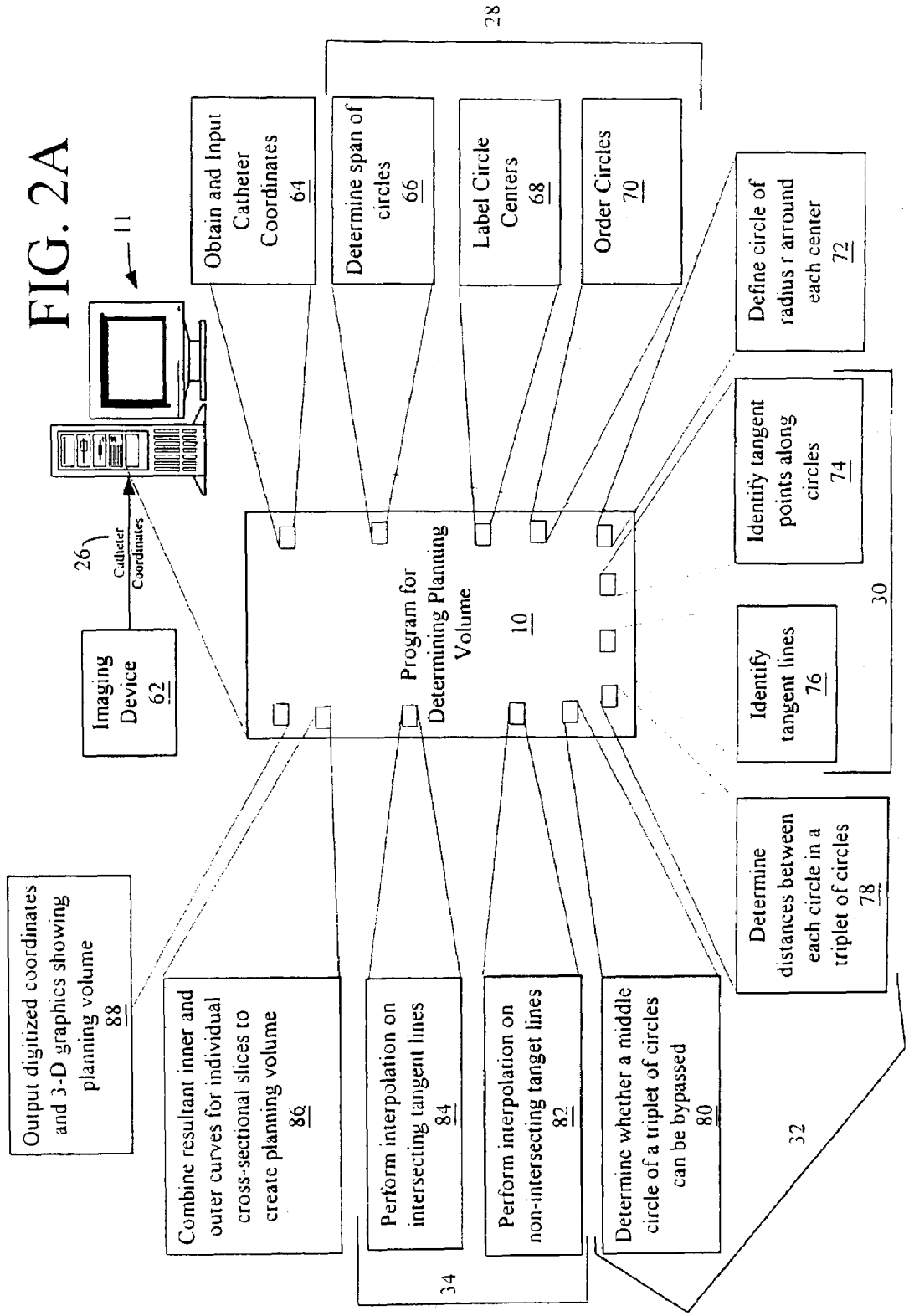
FIG. 2A is a block diagram illustrating an imaging device and its input into a computer, and further illustrating the automated planning volume system and the steps executed thereby to generate the planning volume.

FIG. 2A illustrates one possible configuration of an imaging device 62, for inputting data 26 (i.e. catheter coordinates), with a computer 11, and further illustrates the AVPA program 10 and the steps performed thereby to generate the planning volume 42. Particularly, the AVPA program 10 will perform an initial step of Obtaining the Inputted Catheter Coordinates 64 for analysis. From the input data 26, the program 10 will Determine the Span 66 (or furthest distance between the centers), Label the Circle Centers 68, and Order the Circles 70 into a natural order. Cumulatively these steps (66, 68 and 70) comprise the labeling circle centers and ordering of circles algorithm 28 (see FIG. 2B). Next, a certain radius r is defined about each center 72. With the dimensions of the circles defined, tangent points are identified along the circles 74 and therefrom tangent lines 76 are identified; referred to as the algorithm for Tangent Point Identification 30 (see FIG. 2B). The APVA program 10 then determines the distances between each circle in consecutive triplets of circles 78 in order to ascertain whether a middle circle of each consecutive triplet of circles may be bypassed 80 for a particular interpolation. Together steps 78 and 80 comprise the Determine Bypassing Circles algorithm 32 (see FIG. 2B). For interpolation, the tangent lines are separated into intersecting and non-intersecting tangent lines. Interpolation is performed on non-intersecting tangent lines 82 and interpolation is also performed on intersecting tangent lines 84, the cumulative curve formed by the interpolation steps is determined in accordance with the Local Interpolation algorithm 34 (see FIG. 2B). Finally, the interpolation data for both inner and outer curves of all cross-sectional slices is combined 86 to generate the planning volume and is outputted in the form of digitized coordinates and graphics 88.

Figure 2B:
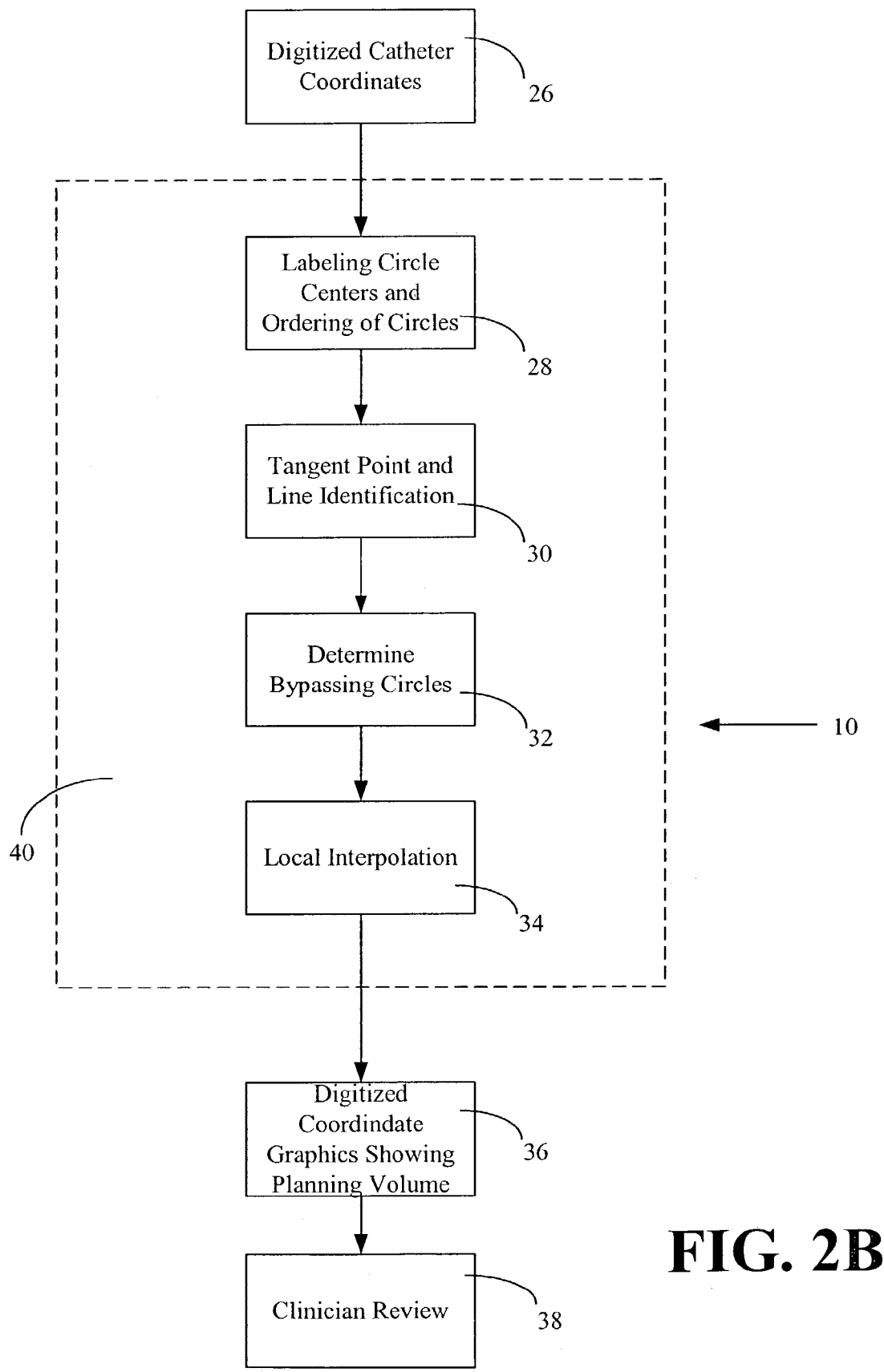
FIG. 2B is a block diagram showing the algorithmic steps of the automated planning volume system of FIG. 1.

As shown in FIG. 2B, the APVA system 10 consists of a series of algorithms which utilize the input data 26 (i.e. digitized catheter coordinates) to calculate the planning volume 42. The steps of the APVA system 10 include Ordering of Circles 28, the Identification of Tangent Points 30, the Determination of Bypassed Circles 32, and Local Interpolation 34. These steps occur in essentially a "black box" 40 and are automatically calculated by the APVA algorithms. The output 36 (i.e. digitized coordinates and graphics showing the planning volume) is thus automatically generated by the APVA system 10 from the input data 26. The output 36 is evaluated and approved during a clinician review 38.

Figure 3:
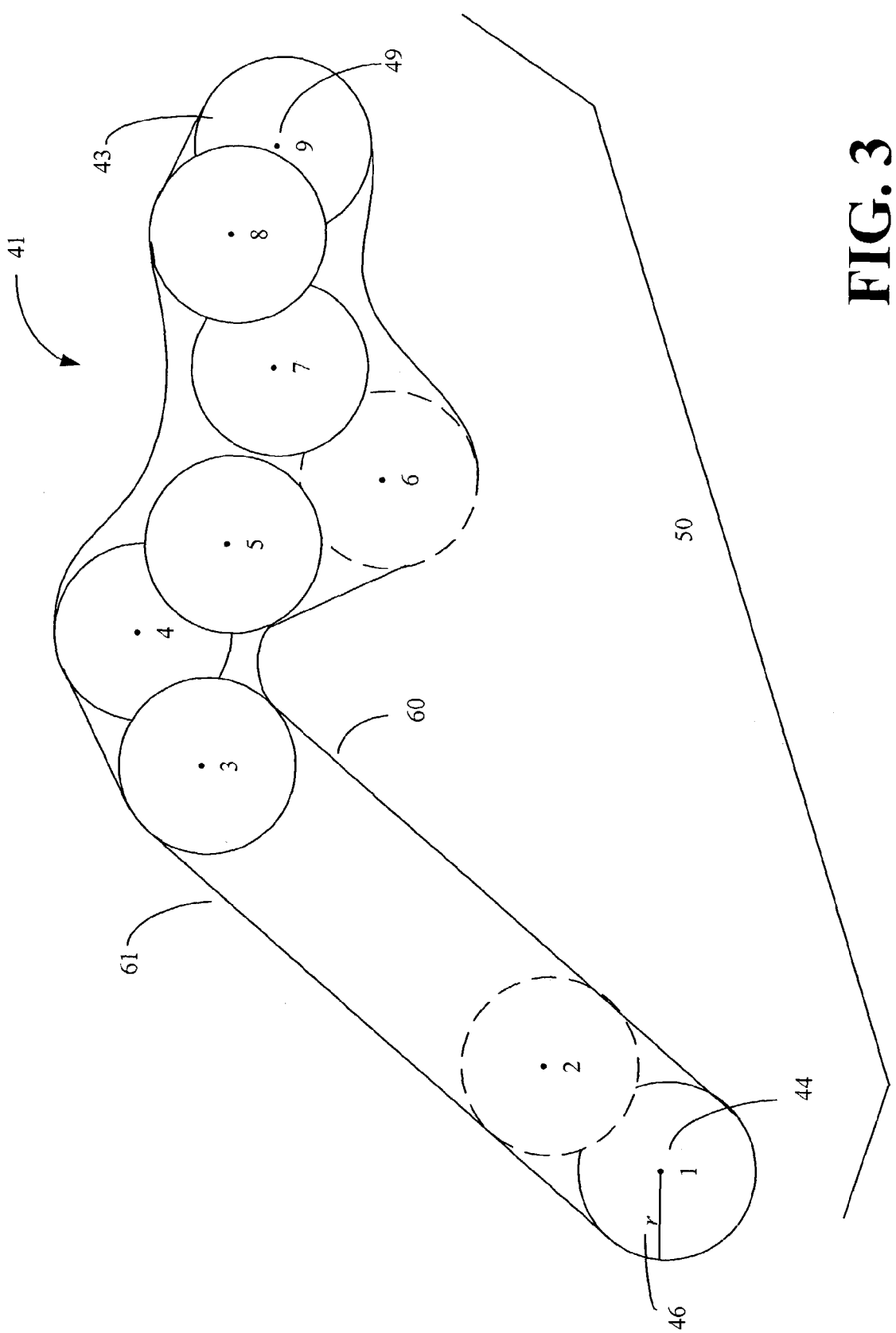
FIG. 3 is a graphical representation of a cross-sectional slice showing nine catheter insertions, circles of radii r around the catheter centers, and the natural ordering of the circle centers from the origin to the destination.

FIG. 3 illustrates a cross-sectional slice 41 of a soft-tissue sarcoma on the left shoulder of a patient. The catheters inserted during surgery are shown as centers 44 (numbers 1–9) in the cross-sectional slice 41. Around each center 44, a radius r 46 is drawn which represents the target volume as a circle 43. The algorithm begins by determining the "span" 50 of the circle 43 centers 44. The centers 44 are labeled from left to right, starting at the origin and proceeding in natural order to the destination 49. Tissue between adjacent catheters that are more than approximately 1 cm apart is considered part of the tumor bed. In the preferred embodiment, the Labeling Circle Centers and Ordering of Circles 28 is conducted in accordance with the following:

Let n be the number of centers 44 on a cross-sectional slice 41, where p is the parent circle center, i is an indexer, $a_{nil}$ indicates that the circle center as not been labeled and has no parent, t is an indexer, lastindex indicates the last index used, tmpindex indicates a temporary storage index, d is a destination and $c_k$ is the center of the circle that has not been labeled. Assume the centers 44 of the circles 43 are ordered as $c_i, \ldots, c_n$. Denote the circle 43 corresponding to center 44 $c_i$ by $C_i$.

1. Initialization: Set N={1, . . . , n}; p[i]=nil for all i ∈N; $a_{nil}$=; lastindex=o; L={o}; L=N\L; t=1.
2. Iteration t: Find i ∈L such that $a_i$ is closest in Euclidean distance from center $a_{lastindex}$. If $a_{p[lastindex]}-a_i > a_{[lastindex]}-a_i$, set p[i]=lastindex. Otherwise, set p[i]=p[lastindex], tmpindex=p[lastindex], p[lastindex]=p[tmpindex], p[tmpindex]=lastindex.
3. Update: L L\{i}, t t+1, lastindex=i. If L=0, or if lastindex=d, go to step 4. Otherwise, go to step 2.
4. Constructing the labels: Recover the sequence of centers by using p to backtrack. Call the recovered sequence $c_i, \ldots, c_{|\cdot|L}$(Here,| |Ldenotes the number of elements in the set L.)

If L=0, labeling is complete. Otherwise,| |Lcenters, represented by $c_i, \ldots, c_{|\cdot, L|}$ have been labeled and proceed to second-stage correction for the remaining n−| centers in order to verify that all centers have been included. For each remaining center $a_i$, i ∈L, the correction algorithm selects among the labeled centers the one, $c_k$, that is closest to $a_i$.

The center $a_i$ is then inserted either between $c_{k-1}$ and $c_k$ or between $c_k$ and $c_{k+1}$, depending on the distance of $a_i$ from $c_{k-1}$ and $c_{k+1}$.

Figure 4:
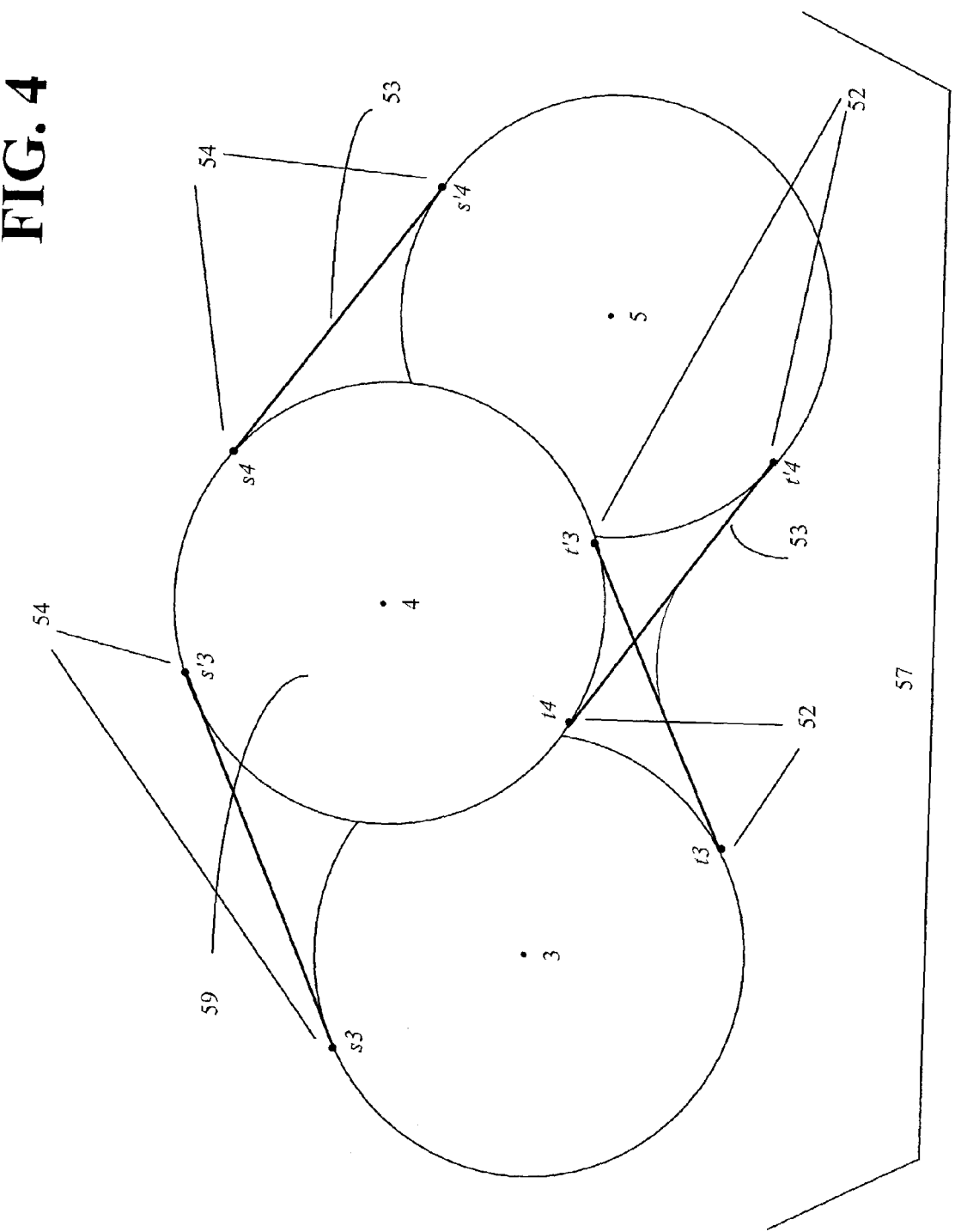
FIG. 4 is a graphical representation of circles 3, 4 and 5 of FIG. 3, illustrating the construction of the tangent points and the corresponding interpolation of the inner curve.

After the centers 44 have been ordered and labeled (i.e. the ordering and labeling of circles 28 as shown in FIG. 2B), the second step of the APVA system 10 is the identification of tangent points 30. FIG. 4 focuses on the 3, 4 and 5 circles 43 of FIG. 4. In the identification of tangent points 30 step, the algorithm constructs tangent points 52 along the circles 43. These tangent points 52 correspond to tangent lines 53. In FIG. 3, the tangent points 52, $t_3$ and $t_3$', on 3 and 4 circles 43 are shown. Some of the tangent points 52 are later used as the interpolation points 54 in the local interpolation step 34. The tangent point identification 30 is accomplished by the following:

For each consecutive pair of circles 43, $C_i$ and $C_{i+1}$, identify a point $t_i$ on $C_i$ and a point $t_i$' on $C_{i+1}$ such that the line segment connecting $t_i$ and $t_i$' is tangent to both circles 43 and parallel to the line segment connecting $C_i$ and $C_{i+1}$, i.e. the tangent line segment 53, $l_i$ of $C_i$ and $C_{i+1}$. The tangent point identification 30 step requires exactly 2(n−1) operations to complete.

Figure 6:
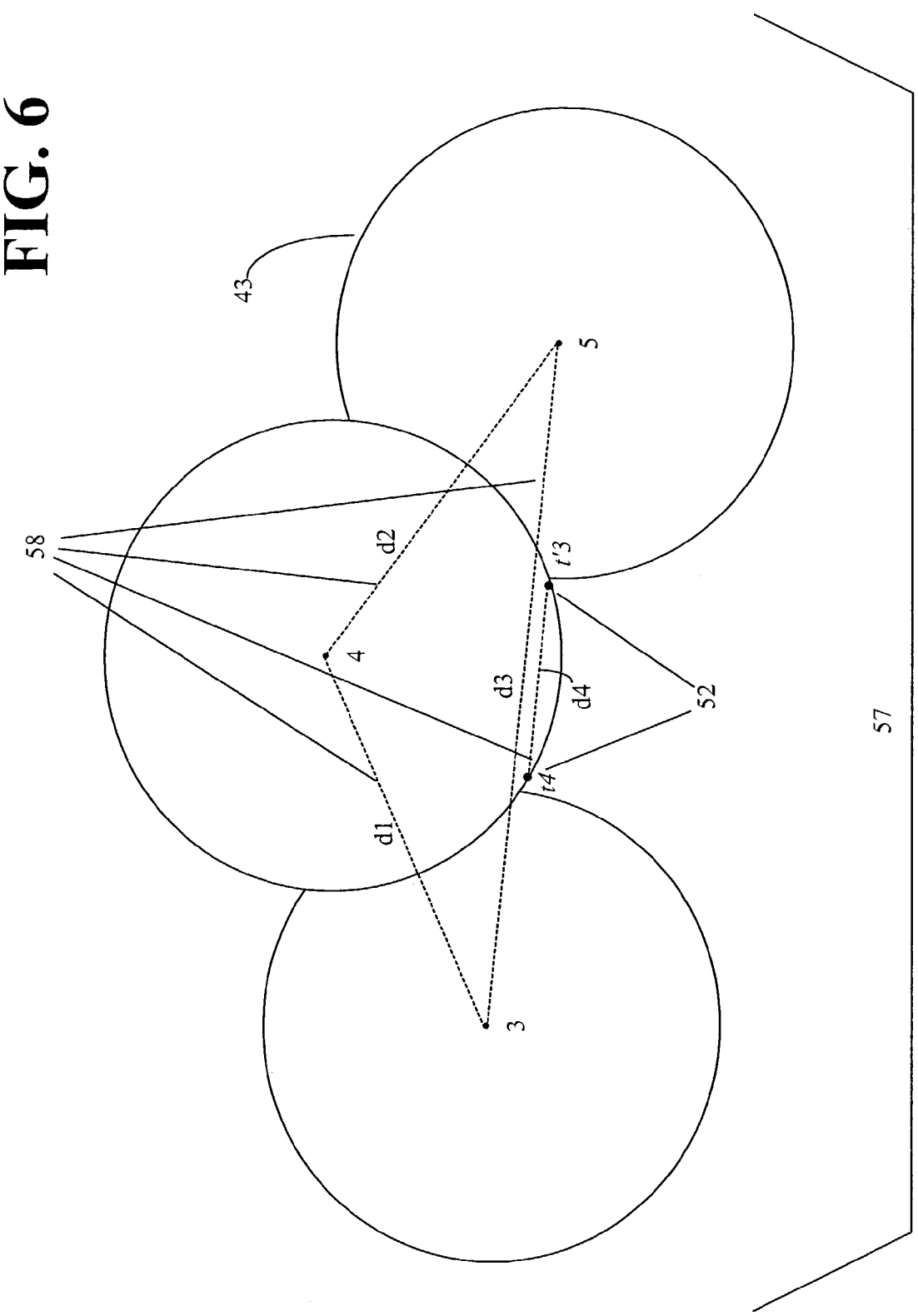
FIG. 6 is a graphical representation of circles 3, 4 and 5 of FIG. 3, illustrating the attributes used to determine whether a middle circle should be bypassed.
Figure 7A:
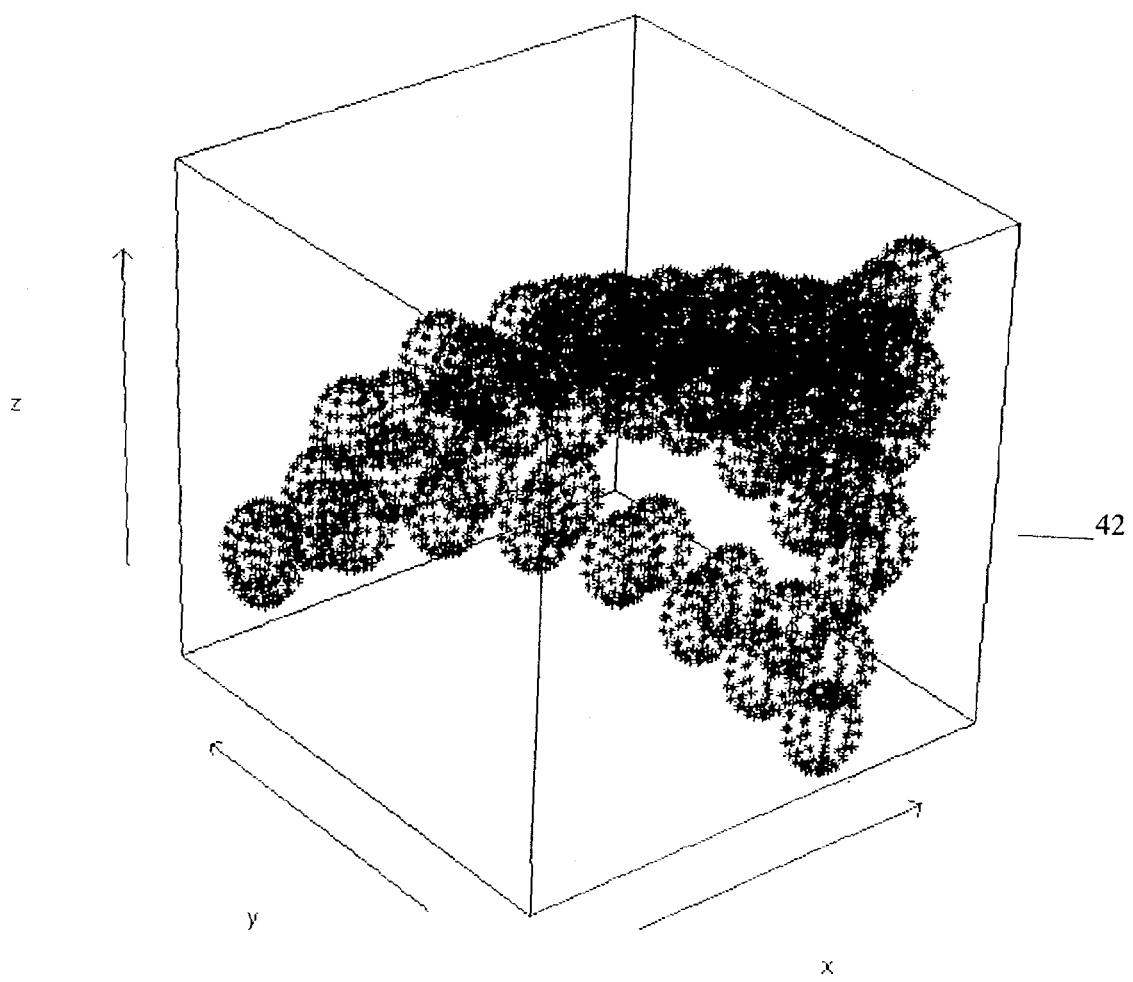
FIGS. 7A–7F are three-dimensional graphical representations (in six rotations of axis) of the resultant planning volume of a sarcoma.
Figure 7B:
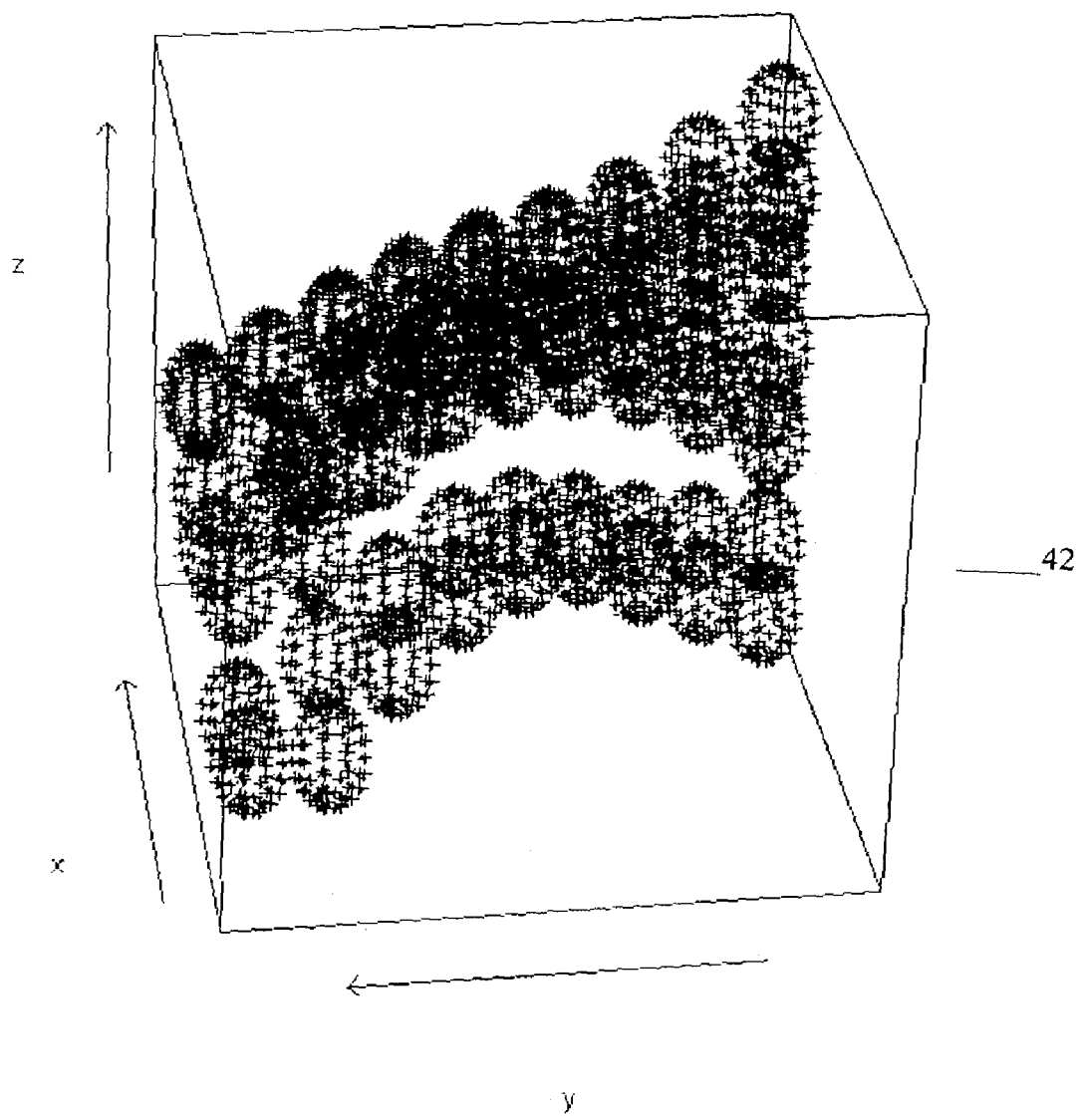
Figure 7C:
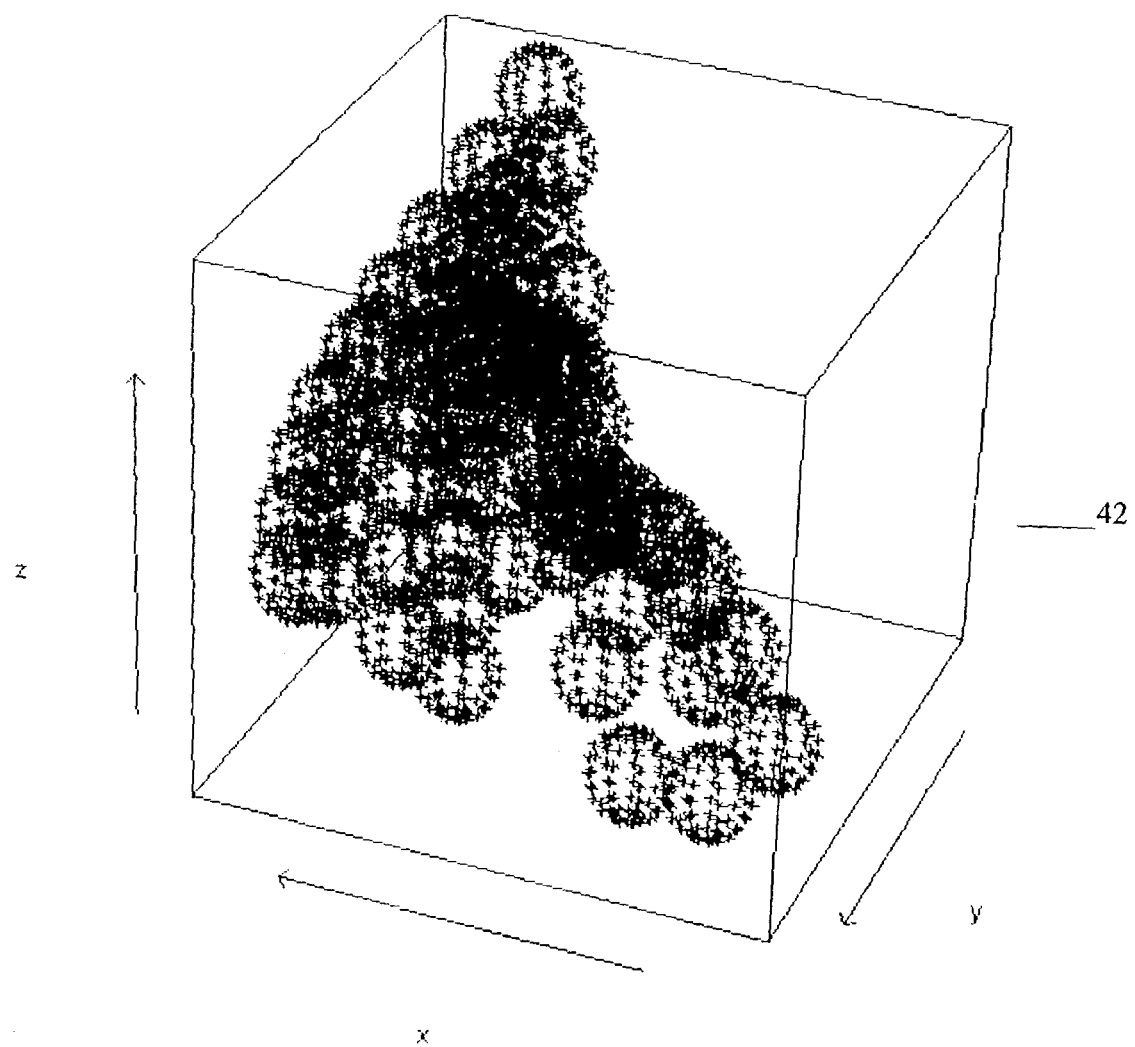
Figure 7D:
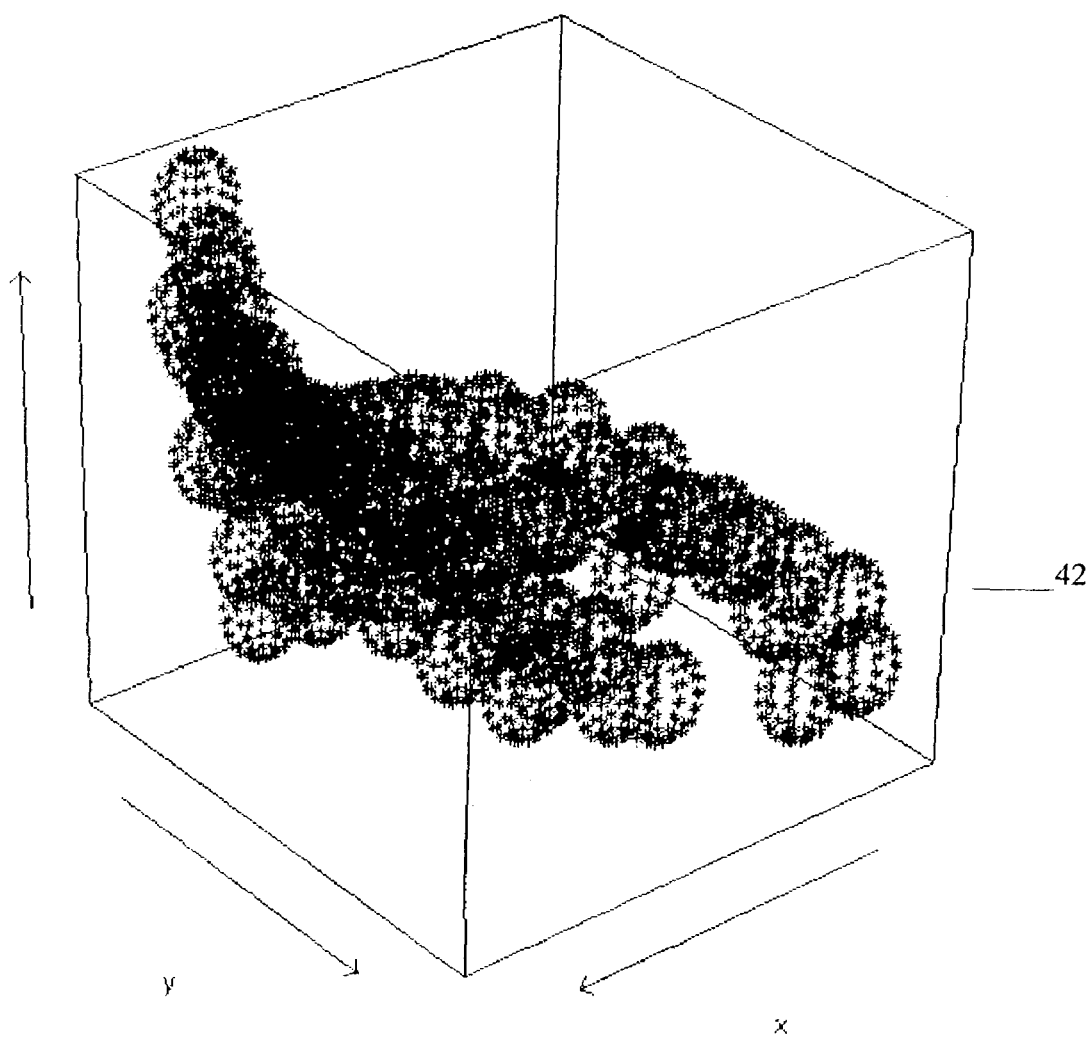
Figure 7E:
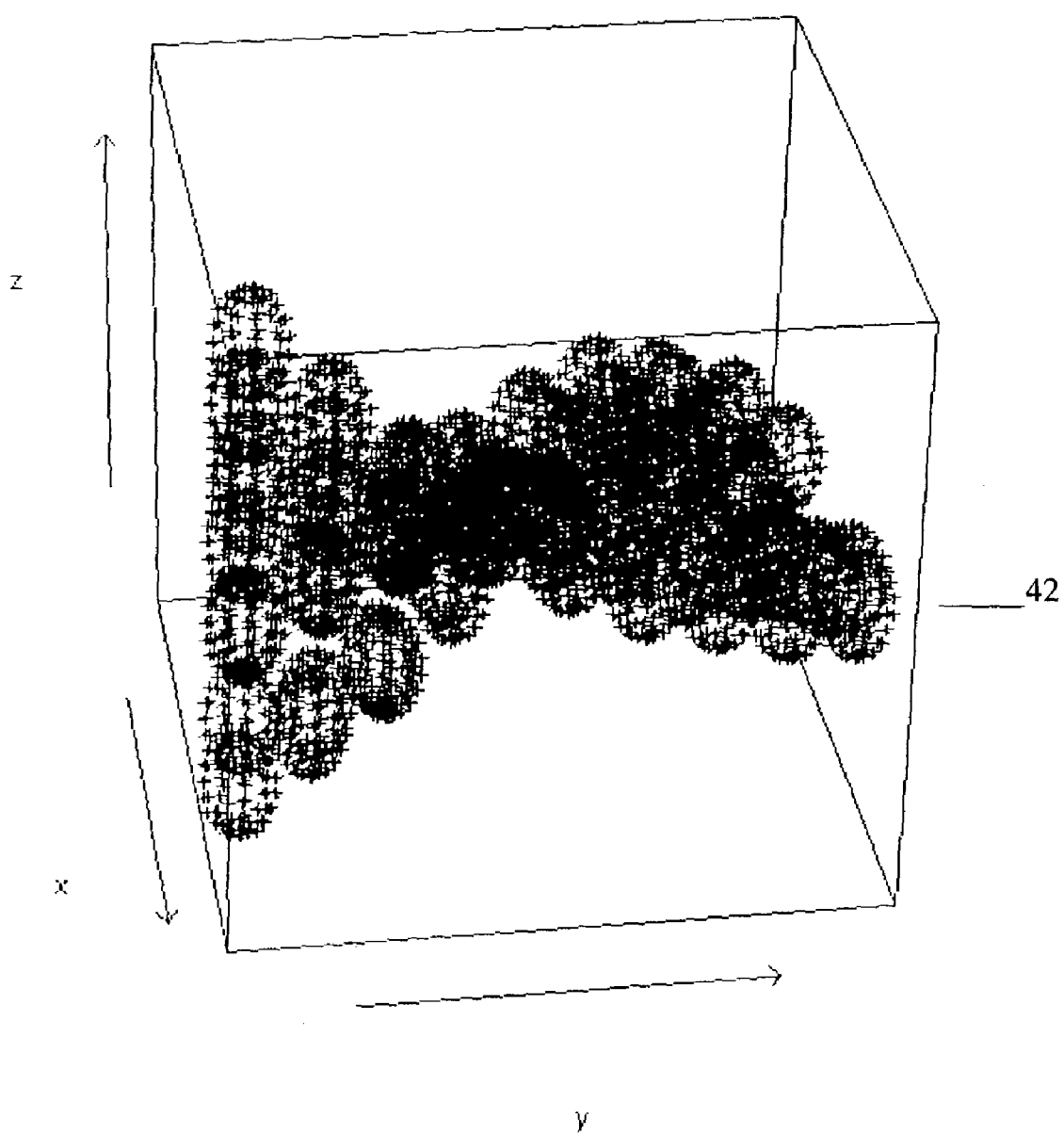
Figure 7F:
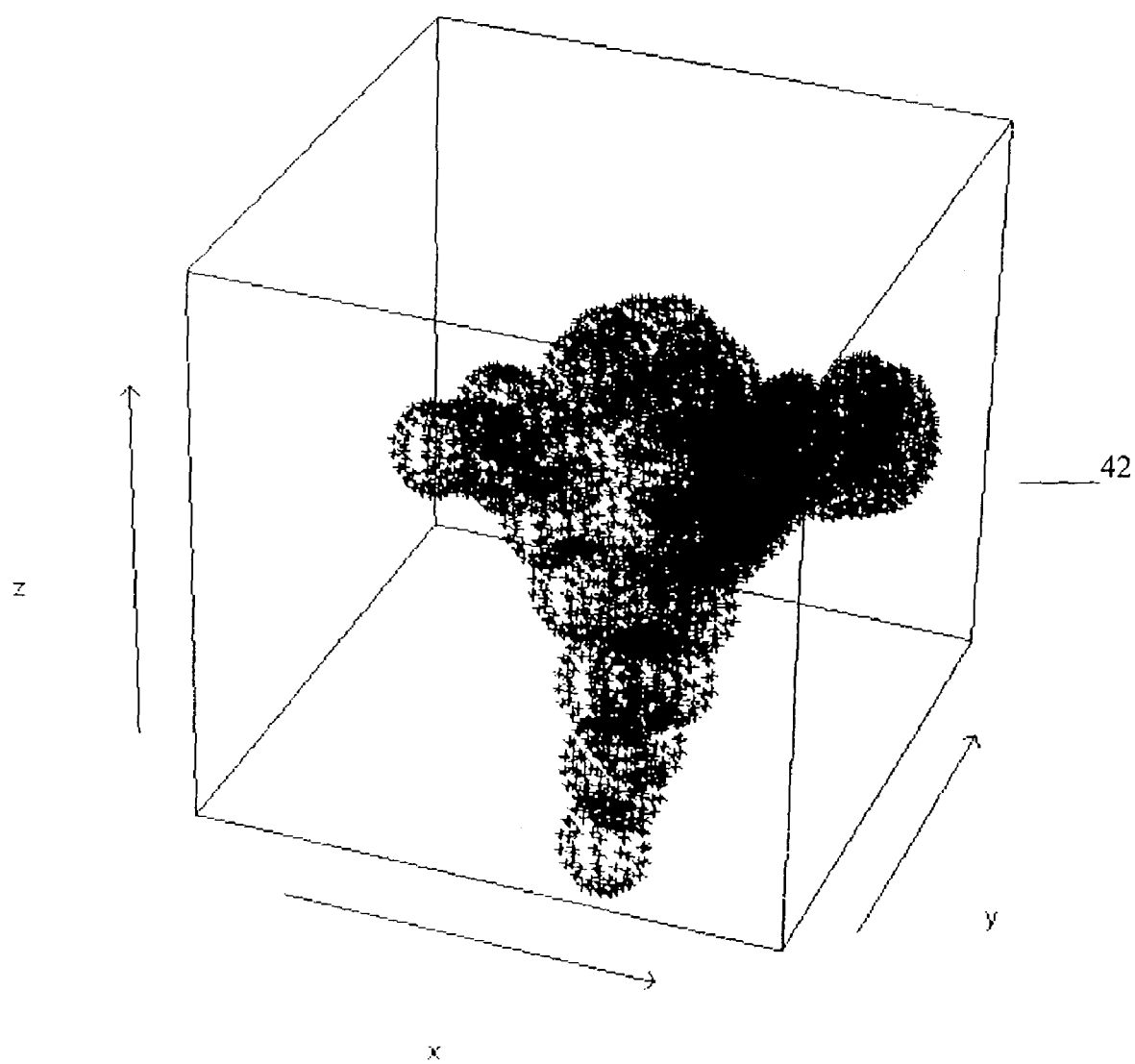

Having established the tangent points 52 and tangent lines 53 for the circles 43, the algorithm then determines whether certain circles 43 may be bypassed for iterations of local interpolation 34 (the determine bypassing circles 32 step (see FIG. 2B)). Each circle 43, out of consecutive triplets of circles 57, is examined to determine if it should be included in the interpolation step 34. FIG. 6 illustrates an instance in which a circle 43 can be bypassed due to the attributes 58 of the spatial relationship between the 3, 4 and 5 circles 43. The attributes 58 indicate the distances between the circles 43 and are labeled as d1, d2, d3 and d4 in FIG. 6. It is shown that the middle circle 59, denoted as circle 4, is bypassed, and that the 3 and 5 circles 43 are included for iterative purposes of local interpolation 34. The algorithm then proceeds to analyze the 3, 5 and 6 circles 43 to determine if the "new" middle circle 59 may be bypassed. Whether a circle 43 may be bypassed 32 is determined in accordance with the following:

The current circle, $C_{i+1}$ (or circle 4 on FIG. 6), is viewed in relation to circles $C_i$ and $C_{i+2}$, where $C_i$ is the highest labeled circle in the sequence not bypassed thus far. For i=1, . . . , n−2 triplets of circles 57, $C_i$, $C_{i+1}$ and $C_{i+2}$, artificial intelligence and machine learning techniques are used to designate which circles 43 may be bypassed. Associated with the circles $C_i$, $C_{i+1}$ and $C_{i+2}$, are tangent points $t_3$' and $t_4$. If the distance between $C_i$ and $C_{i+1}$ and the distance between $C_{i+1}$ and $C_{i+2}$ are both less than 2 r, and the associated tangent points $t_3$' and $t_4$ are within r, then the middle circle 59 is bypassed.

Once the algorithm has determined which circles 43 are to be bypassed 32, the circles 43 are separated into groups of bypassed or non-bypassed circles. The circles 43 that are bypassed are not included in the interpolation step 34 and the circles 43 that are not bypassed are included in the interpolation step 34, such that a smooth curve is maintained for both the inner 60 and outer 61 curves of the planning volume 42. The bypassing step 32 is performed twice in conjunction with the local nonlinear interpolation 34 for the inner 60 and outer 61 curves. Thus, a circle 43 may be bypassed in one curve, but included in the other for interpolation purposes.

Figure 5:
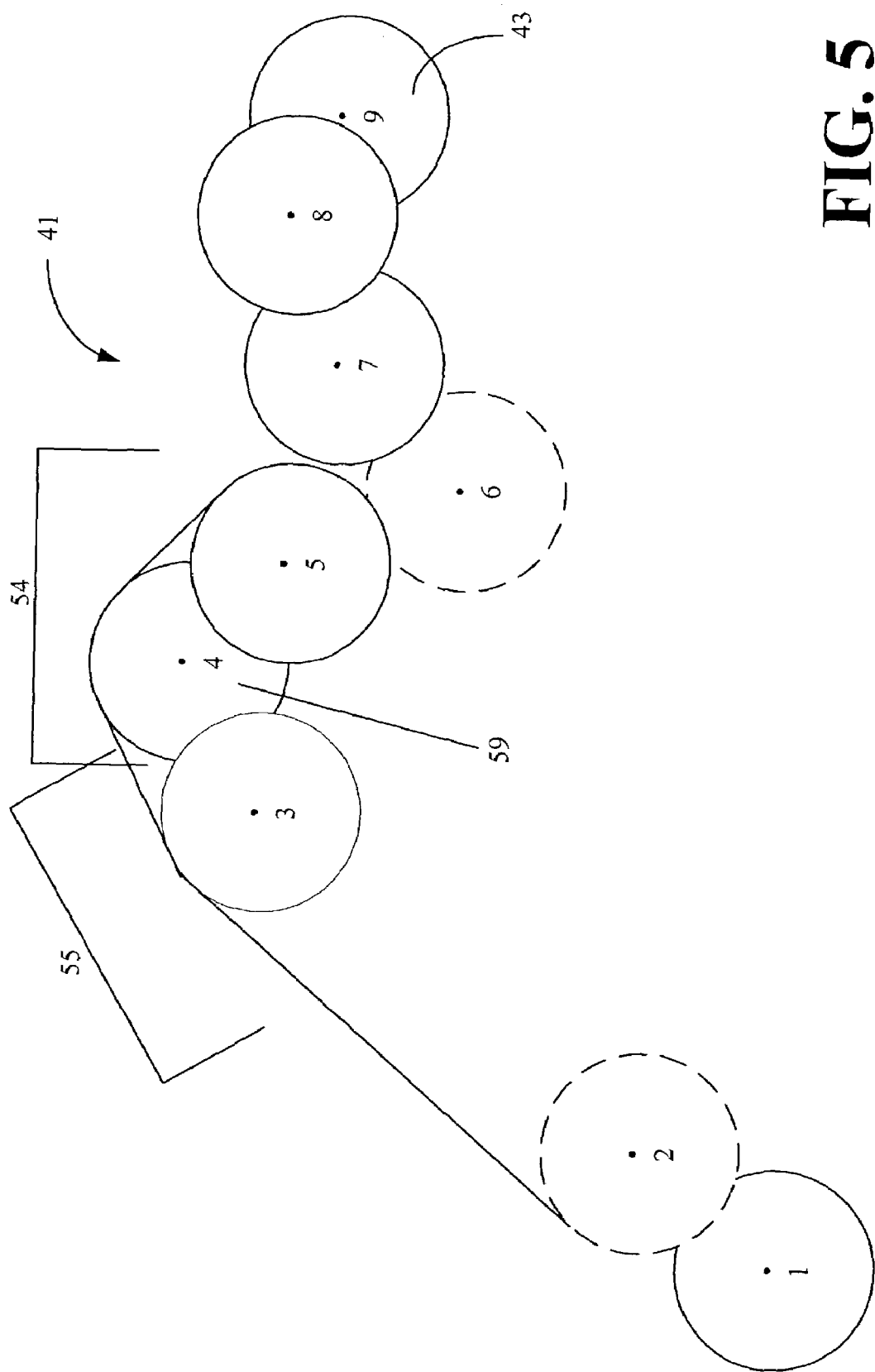
FIG. 5 is a graphical representation focussing on circles 3, 4, 5 and 6 of FIG. 3, illustrating the construction of part of the curve for the planning volume.

The algorithm then performs local interpolation 34 on the consecutive triplets of circles 57, with the last circle 43 of one iteration serving as the first circle 43 of the next iteration. In this manner, the local nonlinear interpolation 34 is performed on consecutive pairs of tangent lines 53 in two phases, the non-intersecting phase and the intersecting phase. In the non-intersecting phase, the non-intersecting tangent line 54 segments are identified and the curve is constructed in accordance with the following:

For consecutive triplets of tangent lines 53, $l_i$, $l_{i+1}$, and $l_{i+2}$, if $l_i$ does not intersect $l_{i+1}$ and $l_{i+1}$ does not intersect $l_{i+2}$, then $l_{i+1}$, plus the arc in the middle circle 59 becomes part of the resulting curve for non-intersecting tangent line phase. The next iteration continues using the tangent lines 53 $l_{i+1}$, $l_{i+2}$, and $l_{i+3}$. FIG. 5 illustrates a non-intersecting iteration on the 3, 4 and 5 circles 43.

In the intersecting phase, the pairs of consecutive intersecting tangent line segments 55 are identified and the curve is constructed in accordance with the following:

For every consecutive pair of tangent lines 53, $l_i$ and $l_{i+1}$, that intersect, nonlinear interpolation is performed using one point (interpolation point 54) on each tangent line 53 and their intersection point. Specifically, recall $t_i$ and $t_i^1$ are the tangent points 52 for $l_i$ on circles $C_i$ and $C_{i+1}$, respectively. If $l_i$ does not intersect with $l_{i-1}$, then $t_i$ will be chosen for interpolation for tangent line 53 $l_i$, otherwise, the mid-point between $t_i$ and $t_i^1$ will be used. Similarly, if $l_{i+1}$ does not intersect with $l_{i+2}$, then $t_{i+1}^1$ will be used. Otherwise, the midpoint of $t_i^1$ and $t_{i+1}^1$ will be employed. The curve obtained from the interpolation constitutes the curve for the tumor surface around these circles 43. FIG. 5 illustrates an intersecting iteration on the 2, 3 and 4 circles 43.

The iterations will continue until $C_n$ is employed in the interpolation, at which point the iteration should stop. It is possible that the final iteration will include only two circles 43 for a local interpolation 34, in which case the local curve is simply the tangent line 53 connecting the two circles 43.

The local interpolation 34 step is performed twice so as to generate the inner 60 and outer 61 curves (see FIG. 3) along the circles 43 of the planning volume for each cross-sectional slice 41. The cumulative collection of curves 60, 61 resulting from the local interpolation 34 step specifies the contours of the tumor bed. From the iterative process of interpolation, the algorithm generates, without any human intervention, an output 36 consisting of the digitized coordinates and graphics which define the planning volume 42 for each slice 41. Examples of the three dimensional graphical output of the planning volume 42, rotated through six axis, are shown in FIGS. 7A–7F. Finally, the output 36 from the APVA algorithm 10 is evaluated and approved by a clinician (see 38 on FIG. 2B).

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A computer readable medium having computer-executable instructions for automatically determining a planning volume of a sarcoma said computer-executable instructions, comprising:

means for locating catheter coordinates for catheters inserted into the sarcoma, where the catheters are configured as centers in cross-sectional slices of the sarcoma;

means for inputting the catheter coordinates;

means for selecting circles of radius r about the centers;

means for labeling the centers and ordering the circles;

means for identifying tangent points and corresponding tangent lines;

means for determining whether a circle should be included in or omitted from interpolation to determine the planning volume;

means for performing local interpolation on the circles;

means for generating digital coordinates and graphical outputs showing the planning volume; and means for evaluating the planning volume outputs.

2. The computer readable medium of claim 1, wherein the means for locating catheter coordinates for catheters inserted into the sarcoma comprises the use of an imaging device to generate a series of films showing the positions of the catheters within the sarcoma.

3. The computer readable medium of claim 2, further comprising the digitization of the catheter coordinates.

4. The computer readable medium of claim 1, wherein the means for selecting circles of radius r about the centers further comprises selecting the radii such that the circles substantially cover surfaces of the cross-sectional slices of the sarcoma.

5. The computer readable medium of claim 1, wherein the means for labeling of centers and ordering of circles comprises an algorithm having four phases, the phases consisting of initialization, iteration t, update and construction of labels, and is of the formula:

Initialization: Set $N=\{1, \ldots, n\}$; $p[i]$=nil for all $i \in N$; $a_{nil}=\infty$, lastindex=o; $L=\{o\}$; $L=N\backslash L$; $t=1$;

Iteration t: Find $i \in L$ such that $a_i$ is closest in Euclidean distance from center $a_{lastindex}$. If $\|a_{p[lastindex]}-a_i\|> \|a_{[lastindex]}-a_i\|$, set $p[i]$=lastindex. Otherwise, set $p[i]$=p[lastindex], tmpindex=p[lastindex], p[lastindex]=p[tmpindex], p[tmpindex]=lastindex;

Update: $L \leftarrow L\backslash\{i\}$, $t \leftarrow t+1$, lastindex=i. If $L=0$, or if lastindex=d, go to Construction of labels. Otherwise, go to iteration t;

Construction of labels: Recover the sequence of centers by using p to backtrack, the recovered sequence being $c_i, \ldots, c_{|L|}$;

where n is the number of centers on the cross-sectional slice, p is the parent circle center, i is an indexer, $a_{nil}$ indicates that the circle center as not been labeled and has no parent, t is an indexer, lastindex indicates the last index used, tmpindex indicates a temporary storage index, d is a destination, $c_k$ is the center of the circle that has not been labeled, and where the centers of the circles are ordered as $c_i, \ldots, c_n$, and the circles corresponding to the centers are denoted as $C_i$, and |L| denotes the number of elements in the set L.

6. The computer readable medium of claim 5, wherein if $L=0$, labeling of the centers and ordering of the circles is complete.

7. The computer readable medium of claim 5, wherein if $L \neq O$, the labeling and ordering algorithm performs a second-stage correction for centers n–L wherein a remaining center $a_i$, $i \in L$, is inserted between the closer of ($c_{k-1}$ and $c_k$) or ($c_k$ and $c_{k+1}$).

8. The computer readable medium of claim 1, wherein the means for identifying tangent points and corresponding tangent lines comprises a mathematical determination of a tangent point on each of a consecutive pair of circles.

9. The computer readable medium of claim 8, further comprising instructions for determination of the tangent points such that a resultant line segment connecting the tangent points is tangent to both of the circles and parallel to a line segment connecting the circles.

10. The computer readable medium of claim 1, wherein the means for determining whether a circle should be included in or omitted from interpolation to determine the planning volume comprises an algorithm which examines distances between each circle in a consecutive triplet of circles.

11. The computer readable medium of claim 10, further comprising instructions for the omission of the middle circle from the interpolation where:

the distance between the middle circle and each of the other two circles of the triplet of circles is less than 2 r; and the distance between the middle circle and tangent points of the triplet of circles is less than r.

12. The computer readable medium of claim 1, wherein the means for interpolation on the circles comprises an interpolation algorithm performing iterations on consecutive triplets of circles.

13. The computer readable medium of claim 12, wherein the iterations are performed such that a last circle of one iteration serves as a first circle of a next iteration.

14. The computer readable medium of claim 12, further comprising instructions for:

performance of the local interpolation on consecutive pairs of tangent lines, the tangent lines corresponding to the consecutive triplets of circles; and performance of the local interpolation in an intersecting phase and a non-intersecting phase.

15. The computer readable medium of claim 14, wherein the non-intersecting phase comprises:

identification of tangent line segments that do not intersect;

constructing a curve from the non-intersecting tangent line segments and a portion of an arc in a middle circle of the triplet of circles.

16. The computer readable medium of claim 14, wherein the intersecting phase comprises:

identification of tangent line segments that do intersect;

performing nonlinear interpolation using a point from each of the intersecting tangent line segments and the point of intersection of the intersecting tangent line segments; and constructing a curve from the interpolation which constitutes the curve around the triplet of circles.

17. The computer readable medium of claim 1, wherein the means for interpolation on the circles comprises an interpolation algorithm performing iterations on consecutive triplets of circles, and further comprising:

performing the local interpolation a first time to construct an inner curve along the circles;

performing the local interpolation a second time to construct an outer curve along the circles; and combining the inner and outer curves so as to specify the planning volume of the sarcoma.

18. The computer readable medium of claim 1, wherein the means for generating digital coordinates and graphical outputs showing the planning volume comprise a conversion of mathematical data into pictorial representations of the planning volume and locations of the catheters.

19. The computer readable medium of claim 1, wherein the means for evaluating the planning volume outputs comprise review and evaluation of digital coordinates and graphical data by a clinician.

20. A computer readable medium for automatically determining planning volumes of sarcomas for brachytherapy treatment, comprising:
   logic configured to receive digital input data relating to a catheter coordinate that defines the location of a radiation dispensing catheter; and
   logic configured to execute a geometric algorithm from the input data, to automatically determine a planning volume of a sarcoma.

21. The computer readable medium of claim 20, wherein the logic configured to determine the planning volume further comprises:
   logic configured to construct at least one circle from a cross-section of the sarcoma, wherein the circle is centered around the catheter, and has a predefined radius;
   logic configured to construct at least one tangent line on each circle that comprises the planning volume;
   logic configured to determine whether any circle may be bypassed, based on the spatial relationship between consecutive circles; and
   logic configured to generate contours of the planning volume.

22. The computer readable medium of claim 20, wherein the planning volume is derived from a tumor bed.

* * * * *

UNITED STATES PATENT AND TRADEMARK OFFICE
CERTIFICATE OF CORRECTION

| | |
|---|---|
| PATENT NO. | : 7,107,089 B2 |
| APPLICATION NO. | : 10/465341 |
| DATED | : September 12, 2006 |
| INVENTOR(S) | : Eva K. Lee |

It is certified that error appears in the above-identified patent and that said Letters Patent is hereby corrected as shown below:

Title page of patent, item (73): add --Emory University, Atlanta, GA (US)-- starting on the line beneath "Atlanta, GA (US)".

Column 3, line 47 – omit the comma after "Instead".

Column 5, line 36 – omit space between "2" and "r".

Column 10, line 41 – "as" should be replaced with --has--.

Column 11, line 8 – "FIG. 4" should be replaced with --FIG. 3--.

Column 11, line 11 – "FIG. 3" should be replaced with --FIG. 4--.

Column 11, line 49 – omit space between "2" and "r".

Column 12, line 62 – add a comma between "sarcoma" and "said" and omit the comma after "instructions".

Column 13, line 46 – replace "as" with --has--.

Column 14, lines 14 and 15 – omit the space between "2" and "r".

Signed and Sealed this

Eleventh Day of September, 2007

JON W. DUDAS
*Director of the United States Patent and Trademark Office*